United States Patent
Kaneko et al.

(10) Patent No.: US 6,929,598 B2
(45) Date of Patent: Aug. 16, 2005

(54) CATHETER FOR ARTIFICIAL INSEMINATION

(75) Inventors: Satoru Kaneko, Ichikawa (JP); Nobuo Takagi, Osaka (JP)

(73) Assignee: Nipro Corporation, Osaka (JP)

( * ) Notice: Subject to any disclaimer, the term of this patent is extended or adjusted under 35 U.S.C. 154(b) by 0 days.

(21) Appl. No.: 10/431,522

(22) Filed: May 8, 2003

(65) Prior Publication Data

US 2003/0216610 A1 Nov. 20, 2003

(30) Foreign Application Priority Data

May 15, 2002 (JP) ........................................ 2002-139864

(51) Int. Cl.[7] ................................................ A61D 7/00
(52) U.S. Cl. ........................................ 600/35; 604/906
(58) Field of Search .................. 600/33–35; 119/14.21; 604/906

(56) References Cited

U.S. PATENT DOCUMENTS

| | | | |
|---|---|---|---|
| 4,790,814 A | 12/1988 | Fischl et al. | .................. 604/27 |
| 6,623,422 B2 * | 9/2003 | Kamrava | ...................... 600/34 |
| 6,662,750 B2 * | 12/2003 | Anderson et al. | ........... 119/174 |

FOREIGN PATENT DOCUMENTS

| | | |
|---|---|---|
| FR | 2 635 453 A | 2/1990 |
| FR | 2 715 824 A | 8/1995 |
| JP | 9-108235 | 4/1997 |

* cited by examiner

*Primary Examiner*—John P. Lacyk
(74) *Attorney, Agent, or Firm*—Kubovcik & Kubovcik

(57) ABSTRACT

A catheter for artificial insemination which is a hollow cylindrical catheter having open ends at both ends, the catheter comprising a small diameter portion forming a distal end portion, a large diameter portion forming a proximal end portion and a tapered portion connecting the small diameter portion and the large diameter portion, a total inner volume of the catheter being from 0.2 to 1.0 ml.

6 Claims, 4 Drawing Sheets

CATHETER FOR ARTIFICIAL INSEMINATION

BACKGROUND OF THE INVENTION

The present invention relates to a catheter for artificial insemination. More specifically, the present invention relates to a catheter for artificial insemination which is used for sucking in semen, which is collected from humans, washed and concentrated (sperm suspension), and injecting the same into a uterine cavity.

An Assisted Reproductive Technology (ART) such as artificial insemination or in vitro fertilization is a method for bypassing a part or whole of a process in which a sperm travels up a female reproductive route, fertilizes an egg cell and is fused with an egg cell. According to ART, even in a case in which the number of sperm is extremely small in ejaculated semen or a case in which sperm in semen are lacking in an ability to enter into an egg cell by their own power (fertilizability), fertilization is theoretically possible so long as one sperm and one egg cell exist. The sperm used here may be ejaculated sperm, epididymis sperm or testicle sperm.

In ART, it is important to use morphologically normal motile sperm withdrawn from semen in fertilization. Accordingly, the semen is washed and concentrated to selectively collect motile sperm which are used in fertilization.

A method for selectively collecting motile sperm is roughly classified into a method using centrifugation and a method using motility of sperm per se. The method using centrifugation is a method in which semen is laminated on a density gradient material such as sucrose polymer ficoll, modified colloidal silica gel or percoll, the lamination consisting of semen and the density gradient material is centrifuged to provide a continuous density gradient and a layer of a sperm suspension containing motile sperm in the centrifuged lamination is selectively collected. Motile sperm lose cytoplasm during formation and maturation thereof, and they are high in density compared to bacteria having cytoplasm or immotile sperm. In the method using centrifugation, since only motile sperm are concentrated in a deposit, the deposit is collected to enable the selective collection of motile sperm.

Meanwhile, the method using motility of sperm per se includes a swim-up method, a swim-down method and so on. The swim-up method is a method in which the sperm suspension obtained by the method using centrifugation or the like is allowed to stand in a culture solution and sperm swimming up in the culture solution by their own motility are recovered. The swim-down method is a modified method of the swim-up method used in a case that semen is found defective.

In order to inject the sperm suspension obtained by the foregoing method into a uterine cavity, a fertilization needle made of metal has so far been used. This fertilization needle is used for sucking in a sperm suspension from a distal end side of the needle with a syringe connected with a proximal end side of the needle. The sperm suspension sucked in the syringe is injected from the distal end side of the needle while the distal end side is inserted into a uterine cavity from a vagina via a uterine cervix. Further, a fertilization needle (catheter) made of a flexible material is also used instead of the fertilization needle made of metal.

In many of these conventional fertilization needles, a distal end of the needle is closed and a side hole is formed in a section of a distal end side of the needle. Such a needle does not have a likelihood that, when the distal end of the needle is open, foreign matter in a vagina, vaginal secretions and the like might intrude in the needle from the open end to clog an injection route for a sperm suspension. However, the fertilization needle having such a structure cannot suck or draw in, when sucking a sperm suspension stored in a container such as a test tube, a total amount of the sperm suspension in the container. Even though the suspension is sucked in by inclining the container, the procedure is troublesome and a slight amount of the suspension remains in the container.

Further, since the fertilization needle is used to suck a sperm suspension into a syringe connected with a proximal end portion of the needle, the role of the needle itself is only to pass the suspension. Accordingly, the fertilization needle is formed with a small outer diameter and has a small inner volume because the highest priority is easy insertion into a uterine cavity. Nevertheless, a total amount of a sperm suspension sucked into the syringe is actually not discharged into a uterine cavity and a slight amount of the suspension remains in a connected portion between the syringe and the needle. The suspension remaining in the connected portion while sucking in and injecting can cause a serious problem of reducing the probability of pregnancy particularly in a case that only a small amount of semen is collected.

Moreover, in a fertilization needle having such a small outer diameter, a space is formed between the needle and a wall of a uterine cervix in insertion of the needle into a uterine cavity. As a result, there is a likelihood that a sperm suspension flows out of a uterine os during a procedure of injecting the sperm suspension. Accordingly, a method has been studied in which a flange is mounted on a proximal end portion of the fertilization needle and closely attached to a uterine os while injecting the suspension to prevent outflow of the suspension (Japanese Patent No. 2681345, et al.). However, in the fertilization needle having such a structure, the number of parts is increased, which makes it more difficult to manufacture the fertilization needle and increases the cost of the fertilization needle.

SUMMARY OF THE INVENTION

Under the foregoing circumstances, the present invention aims to provide a catheter for artificial insemination in which an amount of liquid remaining in the catheter after injection is small. Due to the catheter of the present invention, a total amount of a sperm suspension obtained by washing and concentrating semen and stored in a container can be sucked into the catheter and the total amount of the suspension in the catheter can be injected into a uterine cavity. Furthermore, the catheter of the present invention has a simpler structure capable of preventing the sperm suspension from flowing out of a uterine os while injecting the suspension.

The present inventors have assiduously conducted investigations to solve the problems described above. As a result, they have found that use of a catheter having an inner volume capable of storing a total amount of a sperm suspension that is sucked in makes it possible that an amount of the suspension remaining in the catheter is minimized and a nearly total amount of the suspension collected in the catheter is injected into a uterine cavity. Besides, by forming a tapered portion at an intermediate portion of the catheter, a catheter having such a tapered portion prevents the outflow of the suspension from a uterine os without a need of special parts.

That is, the invention is a catheter for artificial insemination which is a hollow cylindrical catheter having open ends at both ends, the catheter comprising a small diameter portion forming a distal end portion, a large diameter portion forming a proximal end portion and a tapered portion connecting the small diameter portion and the large diameter portion, a total inner volume being from 0.2 to 1.0 ml.

DESCRIPTION OF THE DRAWINGS

The catheter for artificial insemination of the present invention is described in detail below by referring to preferred embodiments shown in the appended drawings. However, the invention is not limited to these descriptions.

DETAILED DESCRIPTION OF THE INVENTION

Figure 1:
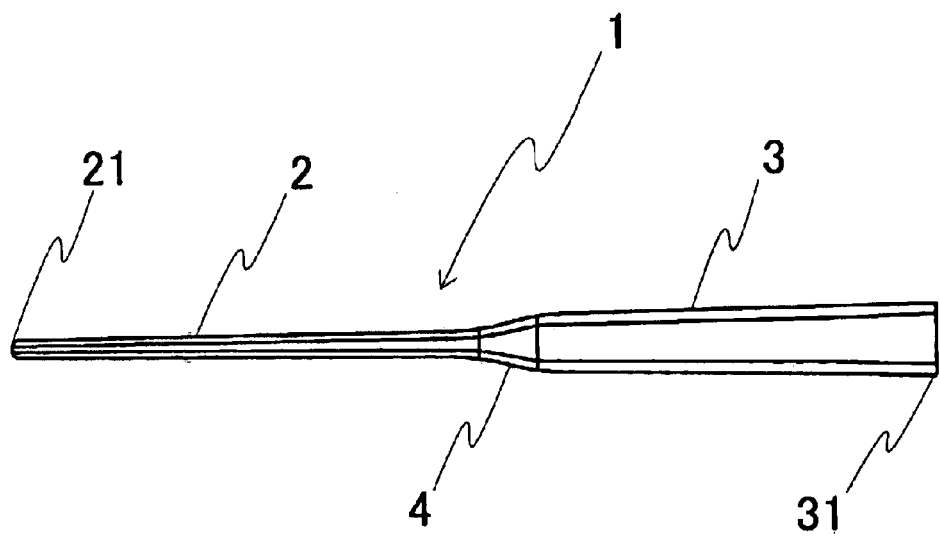
FIG. 1 is a sectional view showing an example of the catheter for artificial insemination of the present invention.

A catheter 1 for artificial insemination of the present invention is a hollow cylindrical catheter having open ends at both ends. The catheter 1 is used for sucking in a sperm suspension obtained by washing and concentrating semen and injecting the suspension into a uterine cavity. The catheter 1 comprises a small diameter portion 2 forming a distal end portion, a large diameter portion 3 forming a proximal end portion, and a tapered portion 4 connecting the small diameter portion 2 and the large diameter portion 3.

The small diameter portion 2 is in a form of a hollow cylinder. The small diameter portion 2 has such a length that a distal opening 21 of the catheter 1 is located inside a uterine cavity when the catheter 1 is inserted into a uterine cervix of a patient. The length is preferably from 30 to 60 mm, more preferably from 40 to 50 mm. When the length is too large, operability during insertion becomes poor. The small diameter portion 2 has such an outer diameter that the small diameter portion 2 can be inserted in a uterine cervix. The outer diameter is preferably from 1.0 to 3.0 mm and, more preferably, from 1.5 to 2.5 mm. When the outer diameter is too small, operability of the catheter 1 becomes poor. The small diameter portion 2 has such an inner diameter that a sperm suspension can be passed through the small diameter portion 2. The inner diameter is preferably from 0.3 to 1.0 mm and, more preferably, from 0.4 to 0.6 mm. A thickness of the wall of the small diameter portion 2 is from 0.35 to 1.35 mm and, more preferably, from 0.5 to 1.0 mm.

The inner diameter of the small diameter portion 2 may be constant over the whole length or, as shown in FIG. 1, may be gradually increased towards a proximal end side of the catheter 1. In the case that the inner diameter of the small diameter portion 2 is gradually increased towards the proximal end side, it is preferable that the outer diameter of the small diameter portion 2 is also increased along with the inner diameter and that the wall thickness is approximately constant, because likelihood of kink is reduced. Further, it is preferable that the distal end of the small diameter portion 2 is formed in a round shape so as not to damage an inner wall of a uterus at the time of insertion of the catheter 1 into the uterus.

Figure 2:
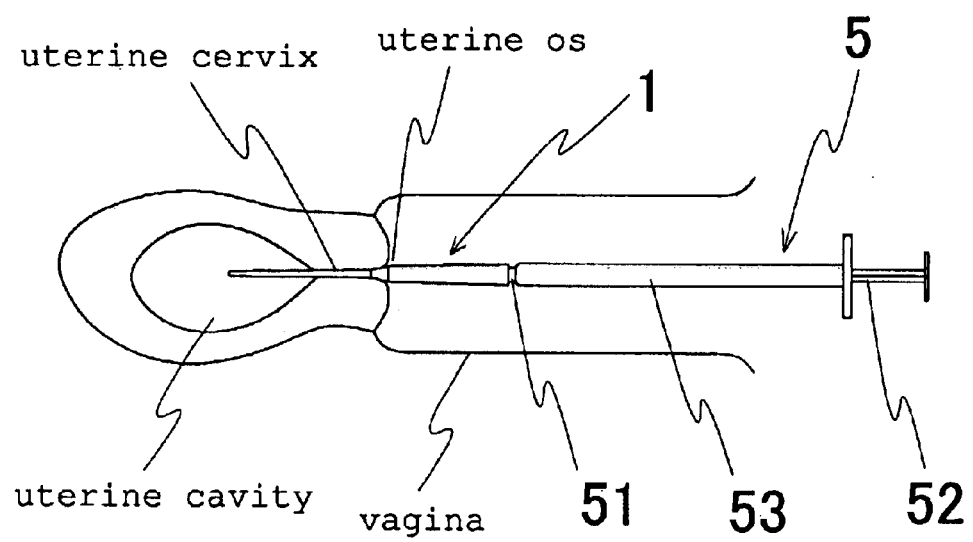
FIG. 2 is a schematic view showing a use example of the catheter for artificial insemination shown in FIG. 1.

The large diameter portion 3 is in a form of a hollow cylinder, and may have such a length that it is easy to operate. The length is preferably from 30 to 70 mm and, more preferably, from 40 to 60 mm. When the length is too large, there is a possibility of kink. When the length is too small, an inner volume is reduced. The large diameter portion 3 has such an outer diameter that it can be inserted into a vagina and hardly be inserted into a uterine cervix. The outer diameter is preferably from 4.0 to 7.0 mm and, more preferably, from 6.0 to 7.0 mm. The large diameter portion 3 has such an inner diameter that a sperm suspension can be passed therethrough. Especially, a proximal opening 31 of the large diameter portion 3 has such an inner diameter that, because a syringe 5 for performing suction and injection of a sperm suspension is connected with the catheter 1 as shown in FIG. 2, a distal end portion 51 of the syringe 5 can be inserted into the proximal opening 31. The inner diameter of the proximal opening 31 of the large diameter portion 3 is preferably from 3.0 to 4.5 mm and, more preferably, from 3.5 to 4.0 mm. A wall thickness of the larger diameter portion 3 is from 0.5 to 2.0 mm and, more preferably, from 0.5 to 1.0 mm.

The inner diameter of the large diameter portion 3 may be constant over the whole length or, as shown in FIG. 1, may be gradually increased towards a proximal end side. In the case that the inner diameter of the large diameter portion 3 is gradually increased towards the proximal end side, it is preferable that the outer diameter of the large diameter portion 3 is also increased along with the inner diameter and that the wall thickness is approximately constant, because likelihood of kink is reduced.

The small diameter portion 2 and the large diameter portion 3 construct the catheter 1 by connection of the proximal end of the small diameter portion 2 and the distal end of the large diameter portion 3 via the tapered portion 4. The tapered portion 4 provides a smooth connection between the small diameter portion 2 and the large diameter portion 3, which differ in outer diameter and inner diameter, without generating a step. The difference in outer diameter of the tapered portion 4 between the distal end and the proximal end thereof is preferably from 2 to 6 mm, more preferably from 4 to 5 mm, and the length of the tapered portion is from 3 to 70 mm and, preferably, 5 to 20 mm. Further, the difference in inner diameter of the tapered portion 4 between the distal end and the proximal end thereof is preferably from 2 to 4 mm, more preferably from 3 to 4 mm.

In a procedure of injecting a sperm suspension, the small diameter portion 2 provided at the distal end of the catheter 1 is inserted into a uterine cervix, and the large diameter portion 3 provided at the proximal end of the catheter 1 is not inserted into a uterine cervix. Accordingly, the tapered portion 4 is positioned to be closely attached to a wall surface in the vicinity of a uterine os. Since the tapered portion 4 does not have a step, the insertion of the catheter 1 can be stopped without damaging a uterine os by the tapered portion 4. It is also possible to prevent a sperm suspension injected into a uterine cavity from flowing out of a uterine os via the uterine cervix in a procedure of injecting the suspension.

With respect to the catheter 1 having the foregoing construction, a total inner volume thereof is preferably from 0.2 to 1.0 ml, more preferably from 0.2 to 0.5 ml. The catheter 1 having such an inner volume in the present invention can store a total amount of the sperm suspension sucked in the catheter 1. Accordingly, an amount of a sperm suspension remaining in the catheter 1 during the suction and the injection of the sperm suspension can be minimized without the sperm suspension entering into a syringe connected with the proximal end side of the catheter 1.

As a material constituting the catheter 1 of the present invention, fluororesins such as PTFE, ETFE and PFA, thermoplastic resins such as polyethylene, polypropylene, polyvinyl chloride and polyurethane, thermosetting resins such as silicone and flexible materials such as thermoplastic elastomer are preferably used. Especially, the catheter 1 made of fluororesins has a high water repellency to more reduce an amount of a suspension remaining in the catheter 1. The catheter 1 also can freely be curved with a hand and the curved shape of the catheter 1 is kept for a long stretch of time. Therefore, the catheter 1 can smoothly be inserted into a uterus upon changing the shape according to a position of a uterine cervix or a uterine cavity of a patient without damaging a uterine inner wall.

As a method for molding the catheter 1, a known method such as extrusion molding or injection molding is used.

A method for using the catheter 1 for artificial insemination of the present invention is described below using FIG. 2.

First, for installing a syringe 5 at a proximal end of the catheter 1, a distal end portion 51 of the syringe 5 is inserted into the proximal opening 31 of the large diameter portion 3. The catheter 1 and the distal end portion 51 of the syringe 5 are securely fixed by fitting. Subsequently, a plunger 52 of the syringe 5 is withdrawn and a sperm suspension in a container is sucked into the catheter 1 from the distal opening 21 of the catheter 1. Since the catheter 1 has a sufficient inner volume to store a total amount of the sperm suspension, the sperm suspension does not intrude into a barrel 53 of the syringe 5. Since the distal opening 21 is located at the end of the catheter 1, the total amount of the sperm suspension in the container, though small, can completely be sucked in. Thereafter, the small diameter portion 2 of the catheter 1 is inserted into a uterine cervix until the tapered portion 4 is brought into contact with a uterine os. At this time, the distal opening 21 of the small diameter portion 2 is located within the uterine cavity and the plunger 52 is pushed to inject the suspension in the catheter 1 into the uterine cavity. Since the tapered portion 4 is closely attached to a wall surface in the vicinity of the uterine os, it is possible to prevent the sperm suspension injected into the uterine cavity from flowing out of the uterine os via the uterine cervix. When the injection of the sperm suspension is completed, the catheter 1 is drawn out of the vagina.

In the above description, the syringe 5 is directly inserted into the proximal opening 31 of the catheter 1. It is also possible to connect the syringe 5 with the proximal opening 31 of the catheter 1 via a stylet.

Figure 3A:
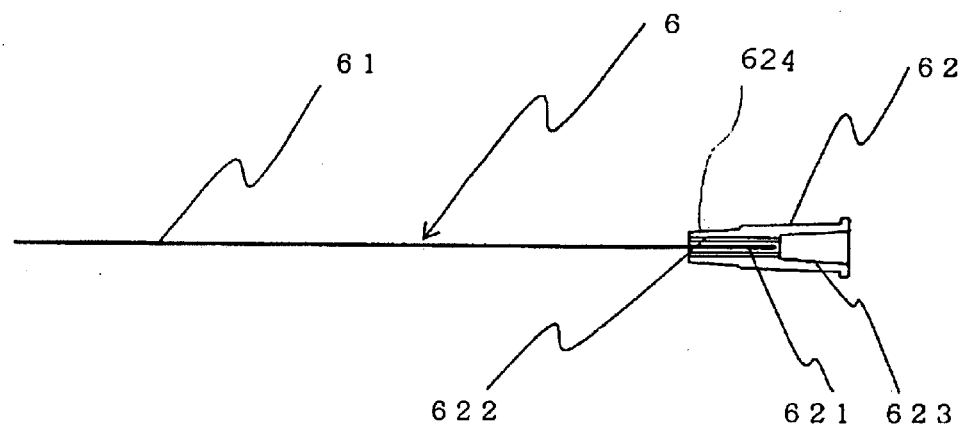
FIG. 3(a) is a sectional view showing an example of a stylet.

A stylet is generally used as an auxiliary tool when it is difficult to insert the catheter 1 into the uterine cavity via the cervical duct. With reference to FIG. 3a, the stylet 6 has a metallic wire 61 which is freely bent by fingers and is capable of maintaining its shape, and a connector 62 at the proximal end of the wire. The metallic wire 61 may or may not be coated by a synthetic resin. The outer diameter of the wire is about 0.2 to about 0.7 mm, and the length of the wire is about 60 to about 120 mm. The connector 62 has a fixed part 621 for adhesively fixing the metallic wire 61, an opening part 622 for passing air or liquid through the stylet 62, and a distal end 624 capable of adhering or mounting in the proximal opening 31 of the catheter 1. The connector 62 has such a shape that the proximal end 623 of the connector 62 can be adhered or mounted with the syringe 5. The material of the connector 62 is polypropylene, polyethylene, polycarbonate, polyvinyl chloride, ABS resin or the like.

Figure 3B:
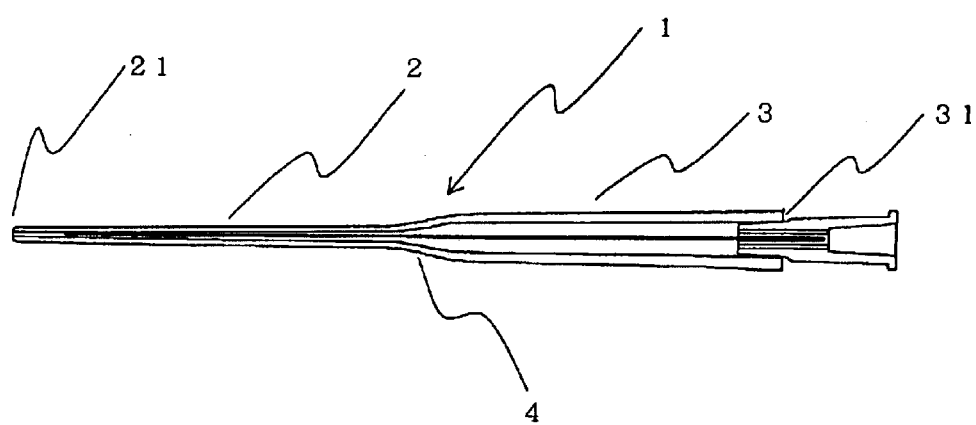
FIG. 3(b) is a sectional view showing an example of the catheter connected with a stylet.
Figure 4:
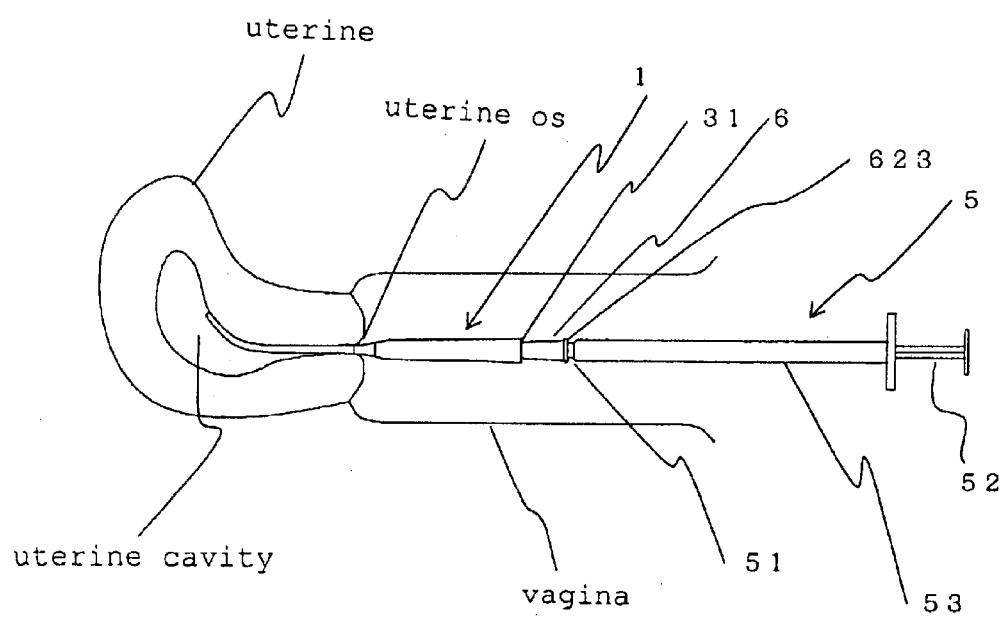
FIG. 4 is a schematic view showing a use example of another catheter for artificial insementation with a stylet and a syringe.

A method for using the catheter 1 with the stylet 62 is described below according to FIGS. 3b and 4.

First, the metallic wire 61 of the stylet 6 is inserted from the proximal opening 31 of the catheter 1 through the large diameter portion 3 forming the proximal end portion of the catheter 1, the tapered portion 4 and then the small diameter portion 2 forming the distal end portion of the catheter 1. The proximal opening 31 of the catheter 1 is then connected with the distal end 624 of the connector 62 of the stylet 6. The distal end of the metallic wire 61 does not necessarily protrude from the catheter 1 but is located inside of the small diameter portion 2, preferably, at a distance of less than 5 mm from the distal end of the small diameter portion 2. In the optional case, the shape of the metallic wire 61 of the stylet 6 is preferably, deformed according to the shape of the uterine cavity in which it is to be inserted. The small diameter portion 2 of the catheter 1 can be bent in a desired shape together with the metallic wire 61 of the stylet 6 after inserting the metallic wire 61 of the stylet 6 into the catheter 1. The bent shape of the small diameter portion 2 of the catheter 1 can allow the catheter 1 to be disposed along the curvature of the uterine cavity.

The syringe 5 is connected with the proximal end 623 of the connector 62 of the stylet 6 after connecting the stylet 6 with the catheter 1. The concentrated and washed sperm in a sperm suspension is slowly sucked using the syringe 5 jointed with the stylet 6 and the catheter 1, and filled into the small diameter portion 2 and, optionally, the tapered portion 4 and the large diameter portion 3. Then, similarly to the catheter in FIG. 2 as described above, the distal opening 21 of the small diameter portion 2 of the catheter 1 is inserted within the uterine cervix to reach the site going across the inlet of the uterine cavity very slowly not so as to damage the uterus. Subsequently, the sperm suspension is injected into the uterine cavity.

In the present invention, the stylet 6 provides such advantages that the insertion is not only easily operated but also performed without any damage of the interior wall of the uterine cavity by bending the metallic wire 61 with the small diameter portion 2 of the catheter 1 if the catheter 1, by itself, is hardly inserted into the uterine cavity or the catheter 1 should be inserted along the interior of the uterine cavity. It is also possible to dispose the catheter 1 along the flexure in the uterine cavity by shaping the small diameter portion 2 of the catheter 1 with the metallic wire 61. Further, it is unnecessary to draw out the stylet 6 from the catheter 1 to ensure the operation because the sperm suspension can be sucked and excreted while the stylet 6 is equipped with the catheter 1.

Effect of the Invention

Since the catheter for artificial insemination of the present invention has an inner volume capable of storing a total amount of a sperm suspension sucked in, an amount of the suspension remaining in the catheter in the procedure of sucking and injecting the suspension can be minimized. Further, since the suction of the sperm suspension is conducted from an opening formed in a distal end of the catheter, it is possible to suck in, even in a case of a small amount of the suspension in a container, a total amount of the suspension. Still further, since the catheter of the present invention has the small diameter portion, the large diameter portion and the tapered portion connecting the small diameter portion and the large diameter portion, it is possible to insert and position the catheter in an appropriate place within a uterus without the need of special parts, and there is no likelihood that a sperm suspension might flow out of the uterus in the procedure of injecting the sperm suspension.

What is claimed is:

1. A catheter for artificial insemination which is a hollow cylindrical catheter having axially extending openings at both ends, the catheter comprising a small diameter portion forming a distal end portion, a large diameter portion forming a proximal end portion and a tapered portion connecting the small diameter portion and the large diameter portion, a total inner volume of said catheter being from 0.2 to 1.0 ml, wherein the tapered portion has a distal end and a proximal end and a difference in inner diameter of the distal end and inner diameter of the proximal end is from 2 to 4 mm, the small diameter portion has an inner diameter of 0.3 to 1.0 mm, and the large diameter portion has an inner diameter of 3.0 to 4.5 mm.

2. The catheter for artificial insemination according to claim 1, wherein a difference in outer diameter of the distal end and outer diameter of the proximal end of the tapered portion is from 2 to 6 mm.

3. The catheter for artificial insemination according to claim 1, wherein the small diameter portion has a length of 30 to 60 mm and an outer diameter of 1.0 to 3.0 mm and the large diameter portion has a length of 30 to 70 mm and an outer diameter of 4.0 to 7.0 mm.

4. A device for artificial insemination comprising the catheter of claim 1 and a syringe having a distal end portion inserted into and connected to the open end of the proximal end portion of the catheter.

5. A device for artificial insemination comprising the catheter of claim 1 and a stylet comprising a metallic wire having a distal end portion and a proximal end portion and connected at the proximal end portion to a connector having an opening for passing air or liquid therethrough, the metallic wire extending through the proximal end portion and the tapered portion of the catheter and into the distal end portion of the catheter and the connector being connected to the open end of the proximal end portion of the catheter.

6. The device of claim 5, further comprising a syringe having a distal end portion fitted to the connector of the stylet.

* * * * *